United States Patent [19]

Vergara et al.

[11] Patent Number: 6,121,213

[45] Date of Patent: Sep. 19, 2000

[54] STABLE PEROXIDE DENTURE PASTE

[75] Inventors: Democrita E. Vergara, Nutley; Michael E. Trama, River Vale; Kuo-Chen Yeh, Westfield, all of N.J.

[73] Assignee: Block Drug Company, Inc., Jersey City, N.J.

[21] Appl. No.: 09/123,345

[22] Filed: Jul. 28, 1998

[51] Int. Cl.$^7$ .............................. A61K 7/30; A61K 7/20; A61K 7/16

[52] U.S. Cl. ................. 510/116; 424/53; 424/57

[58] Field of Search .................................. 510/116, 117; 424/49, 53, 57

[56] References Cited

U.S. PATENT DOCUMENTS

| | | | |
|---|---|---|---|
| 2,498,343 | 2/1950 | Rider et al. | 252/103 |
| 2,498,344 | 2/1950 | Rider et al. | 252/103 |
| 2,576,205 | 11/1951 | Apperson | 252/99 |
| 3,337,466 | 8/1967 | Tuckahoe et al. | 252/99 |
| 3,355,392 | 11/1967 | Cantor et al. | 252/99 |
| 3,595,798 | 7/1971 | Smith et al. | 252/95 |
| 3,936,385 | 2/1976 | Cheng | 252/99 |
| 3,997,459 | 12/1976 | Bogie et al. | 252/99 |
| 4,183,916 | 1/1980 | Rodon | 424/54 |
| 4,490,353 | 12/1984 | Crawford et al. | 424/52 |
| 4,837,008 | 6/1989 | Rudy et al. | 424/53 |
| 4,897,258 | 1/1990 | Rudy et al. | 424/53 |
| 4,925,655 | 5/1990 | Smigel et al. | 424/52 |
| 4,971,782 | 11/1990 | Rudy et al. | 424/53 |
| 5,015,408 | 5/1991 | Reuss | 252/99 |
| 5,041,280 | 8/1991 | Smigel et al. | 424/52 |
| 5,266,305 | 11/1993 | Wood et al. | 424/54 |
| 5,372,803 | 12/1994 | Williams et al. | 424/53 |
| 5,565,190 | 10/1996 | Santalucia et al. | 424/53 |
| 5,599,525 | 2/1997 | Hsu et al. | 424/49 |
| 5,614,174 | 3/1997 | Hsu et al. | 424/49 |
| 5,683,680 | 11/1997 | Santalucia et al. | 424/53 |
| 5,736,158 | 4/1998 | Quast et al. | 424/464 |

OTHER PUBLICATIONS

Poletto, J.F., & Bernstein, S,. United States Statutory Invention Registration No. H83 Jul. 1, 1986 pp. 1–26.

*Primary Examiner*—Yogendra Gupta
*Assistant Examiner*—John M. Petruncio

[57] ABSTRACT

A denture cream for cleaning dentures and removable dental prostheses comprising a peroxide stabilized against chemical degradation by a combination of a bicarbonate and a phosphate, such as an alkali monofluorophosphate.

22 Claims, No Drawings

STABLE PEROXIDE DENTURE PASTE

BACKGROUND OF THE INVENTION

1. Field of the Invention

This invention is directed to a stabilized denture paste or cream and to a method for cleaning dentures using a stabilized denture paste.

2. Description of Related Art

Dentures and other removable full or partial dental prostheses, like the teeth they replace, require regular cleaning to maintain the oral health of the wearer. The considerations that go into designing cleaning compositions for such dental prostheses, however, differ from considerations in designing cleaning compositions for teeth.

Teeth are generally cleaned either by brushing with a dentifrice (or tooth powder) or by rinsing the mouth with a mouthwash. Dentifrices may contain cleansing ingredients, detergents and abrasives. Mouthwashes may contain alcohol or other agents to kill germs in the mouth. An important consideration in formulating a dentifrice or mouthwash, however, is the organoleptic quality of the finished formulation. Another important consideration is the strength of the ingredients used. If the ingredients are too weak, the dentifrice or mouthwash will not clean properly. If the ingredients are too strong, the dentifrice or mouthwash could damage the soft tissues in the mouth.

Dentifrices and mouthwashes may contain other ingredients to strengthen teeth, such as fluorides, hypersensitivity treatments, such as potassium nitrate, or remineralization ingredients, such as hydroxyapatite.

Dental prostheses are typically cleaned either through immersion in a bath containing a cleansing agent or by brushing with a specially formulated cream. Immersion has the advantage of offering complete cleaning, because brushing can miss hard to reach areas of the dental prosthesis. Brushing, however, offers the advantage of both mechanical cleaning and chemical cleaning, and many people prefer brushing with a paste to ensure thorough cleaning of the prosthesis.

Dentures and dental prostheses, however, are not natural teeth. Modern dental prostheses are usually made from polymeric materials. These materials can withstand a high level of cleaning activity, and prostheses do not require any of the special ingredients, such as hypersensitivity ingredients, remineralization ingredients and fluoride treatments, found in dentifrices.

Because of the differing design parameters for denture pastes and dentifrices, many considerations affecting dentifrice formulations are not pertinent for denture pastes.

For example, U.S. Pat. No. 5,372,802 discloses a dentifrice that includes a peroxyacid compound such as hydrogen peroxide, a fluoride-containing anticaries agent and a zinc compound such as zinc citrate. The zinc compound inhibits decomposition that ordinarily would be induced by the presence of fluoride. A denture paste does not need fluoride, since the acrylic polymer of many dental prostheses is not strengthened by fluoride.

Despite the general absence of a need for fluoride in treating dentures and dental prostheses, U.S. Pat. No. 5,736,158 to Quast, issued Apr. 7, 1998, teaches a denture cleanser tablet or paste for partial dental prostheses (that do not replace all teeth in the mouth) containing high levels of fluoride. This fluoride may be sodium fluoride or sodium monofluorophosphate and may be combined with a peroxyacid cleansing agent such as calcium peroxide in a two-layer denture tablet. The fluoride is present at a high level to impregnate the dental prosthesis during cleaning and to leach out during use, thereby providing a fluoride treatment for adjacent natural teeth.

A recent development in dentifrices has been the development of baking soda and peroxide dentifrices. These dentifrices have been formulated in "split tube" designs to prevent reactions between peroxide and baking soda during storage. One example of a split tube dentifrice is found in U.S. Pat. No. 5,599,525 to Hsu et al., issued Feb. 4, 1997. This patent is directed to a split tube configuration having, among other ingredients, calcium peroxide, sodium bicarbonate and a fluoride source such as sodium monofluorophosphate.

Many attempts Wave been made to stabilize the baking soda and peroxide in a single tube configuration. U.S. Pat. No. 4,837,008, for example, discloses an aqueous dentifrice containing a peroxide and/or bicarbonate ingredient. The ingredients are coated to prevent reaction during storage. A disadvantage to such a dentifrice is that release of the ingredients for cleaning effect during use is diminished by the presence of the barrier coating.

Another approach has been stabilizing the formulation by adopting a substantially anhydrous system. U.S. Pat. No. 4,897,258 discloses an anhydrous dentifrice containing calcium peroxide and sodium bicarbonate. The anhydrous state of the dentifrice prevents reaction between the ingredients. A disadvantage to such a dentifrice is that in spite of the anhydrous state of the dentifrice, limited storage ability is experienced. Anhydrous systems might also lead to poor dispersion of the ingredients in the dentifrice itself, and the formulation is expensive compared to water-based dentifrices. U.S. Pat. No. 4,971,782 discloses an anhydrous dentifrice containing peroxide and bicarbonate. One ingredient is coated with a water soluble coating and a peroxide stabilizer is included in the dentifrice to further enhance storage stability. In spite of the presence of the stabilizer, the dentifrice remains deficient in storage stability required for commercial use.

Attempts to stabilize the ingredients in a water-based dentifrice include those discussed in U.S. Pat. No. 5,565,190 to Santalucia et al., issued Oct. 15, 1996, and its divisional patent, U.S. Pat. No. 5,683,680 to Santalucia et al., issued Nov. 4, 1997. These patents disclose sodium hydroxide or sodium carbonate to stabilize a dentifrice composition containing peroxide and bicarbonate. U.S. Pat. No. 5,614,174 to Hsu et al., issued Mar. 25, 1997, is directed to a dentifrice comprising a peroxide, such as calcium peroxide, and sodium bicarbonate. The dentifrice may contain a fluoride source, such as sodium fluoride or sodium monofluorophosphate and the dentifrice is stabilized by the addition of polyethylene glycol 2000.

Other dentifrices have not recognized the problem. U.S. Pat. No. 4,603,045 to Smigel, issued Jul. 29, 1986, for example, is directed to a toothpaste adapted for cleaning natural teeth and bonded composite filling material. The toothpaste contains dicalcium phosphate, calcium carbonate, magnesium carbonate, sorbitol, corn starch, cellulose gum, calcium peroxide, sodium perborate, sodium lauryl sulfoacetate, aluminum hydroxide, saccharinate, flavoring, alkylparaben, sodium monofluoride phosphate, titanium dioxide and water. These ingredients must be present in a carefully balanced combination to achieve the objects of the patent.

U.S. Pat. No. 4,925,655 to Smigel et al., issued May 15, 1990, is directed to a powder composition soluble in water to form a mouthwash. The powder contains calcium peroxide, sodium perborate, sodium bicarbonate, tetrasodium pyrophosphate, sodium lauryl sulfate, sodium sacchrinate, hydrated silica, sodium benzoate, citric acid, flavor, potassium carbonate, tea tree oil, sodium monofluorophosphate, thymol and hexylresorcinol.

U.S. Pat. No. 5,041,280 to Smigel, issued Aug. 20, 1991, is directed to a toothpaste containing dicalcium phosphate, calcium carbonate, sodium bicarbonate magnesium carbonate, sorbitol, corn starch, cellulose gum, calcium peroxide, sodium lauryl sulfoacetate, aluminum hydroxide, sodium saccharinate, flavoring, alkylparaben, sodium monofluorophosphate, titanium dioxide and water.

Despite the recent interest in baking soda and peroxide dentifrices, denture creams have not generally adopted baking soda and peroxide. One attractive feature of baking soda and peroxide dentifrices is that they generate bubbles on use, which gives the user a pleasant sensation. This benefit is lost in denture creams, since cleaning is typically done outside the mouth. Also, the generally stronger cleaning agents used in denture creams can adversely affect the baking soda and peroxide. Stability of denture creams containing such ingredients is difficult to achieve.

SUMMARY OF THE INVENTION

The principal object of the present invention therefore is to provide a denture cream containing baking soda and peroxide stabilized against degradation, especially thermal degradation, during storage.

Another object of the invention is to provide a method for cleaning removable dental prostheses using the denture cream containing baking soda and peroxide.

It is an advantage of the invention that the baking soda and peroxide can be stabilized by a dentifrice ingredient, thereby avoiding the problem of establishing safety information.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and following the purpose of the invention, as embodied and broadly described herein, the invention provides a cream for cleaning removable dental prostheses in association with mechanical scrubbing, comprising a peroxide, a bicarbonate and sodium monofluorophosphate.

To further achieve the foregoing objects and by the purpose of the invention, the invention further provides a method of cleaning a removable dental prosthesis by scrubbing the removable dental prosthesis with a cream comprising a peroxide, a bicarbonate and sodium monofluorophosphate.

DESCRIPTION OF THE PREFERRED EMBODIMENTS

Reference will now be made in detail to the presently preferred embodiments of the invention.

Peroxide compounds can become unstable at elevated temperatures. Dentifrice and denture cream formulations containing peroxides can lose peroxide activity if stored for even limited time at temperatures greater than about 100° F. Stabilizing the peroxide can have a positive impact on denture creams, especially for formulations sold in warm regions.

Denture creams may contain peroxide compounds as cleaning agents, either alone or in combination with other peroxides or other cleaning agents. Preferred peroxides useful in the invention include, but are not limited to, peroxide acids such as hydrogen peroxide, and monovalent and divalent peroxide salts, such as sodium and calcium peroxide. Preferred peroxides include divalent salts such as calcium peroxide. The peroxide may comprise any amount in the cream to accomplish the desired cleaning effect. Generally, however, the peroxide comprises from about 0.1% to about 10% by weight of the cream formulation, preferably from about 0.25% to about 5% by weight and more preferably from about 0.5% to about 2.5% by weight of the denture cream.

The peroxide in the denture cream is stabilized against degradation during shipping and storage by a combination of bicarbonate and monofluorophosphate. This discovery is surprising, since both the bicarbonate and the monofluorophosphate are needed to stabilize the peroxide. If the monofluorophosphate is removed from a formulation otherwise in accord with the invention, then the calcium peroxide decomposes and loses its efficacy as a cleaning and whitening agent. The same holds true if the bicarbonate is absent from a formulation otherwise according to the invention.

The bicarbonate may be any known bicarbonate useful in denture creams, including, but not limited to, potassium bicarbonate and sodium bicarbonate. Sodium bicarbonate, however, is preferred for cost and supply reasons. Preferably, the bicarbonate comprises more of the denture cream formulation than the peroxide on a weight basis. More preferably, the bicarbonate will be present in a weight ratio to the peroxide from about 2:1 to about 10:1, and most preferably from about 2:1 to about 5:1. Thus, if the peroxide is within its preferred range of from about 0.5% by weight to about 2.5% by weight of the denture cream, the bicarbonate will comprise from about 1% by weight to about 25% by weight of the denture cream, more preferably from about 1% by weight to about 10% by weight of the denture cream and even more preferably about 5% by weight of the denture cream.

The monofluorophosphate is preferably sodium monofluorophosphate, although other known cations and ligands, especially alkali cations, may be associated with the monofluorophosphate. The monofluorophosphate preferably comprises less of the denture cream than the bicarbonate and the peroxide on a weight basis. Preferably the monofluorophosphate is present in a weight ratio to the peroxide of from about 0.1:1 to about 1.6:1, and more preferably from about 0.3:1 to about 0.8:1. If the peroxide is present in the denture cream in its preferred range of from about 0.5% by weight to about 2.5% by weight of the denture cream, the monofluorophosphate preferably comprises from about 0.4% to about 0.8% by weight of the denture cream.

Although sodium monofluorophosphate is the most preferred stabilizing agent, other phosphates such as tetrapotassium pyrophosphate, tetrasodium pyrophosphate, and trisodium phosphate may also be used to stabilize the peroxide in the formulations.

The denture cleanser formulation may also contain additional ingredients, including water, glycerin, humectants such as propylene glycol and polyethylene glycol, abrasives, such as silicon dioxide and hydrated silica, detergents and surfactants such as sodium lauryl sulfate, thickeners, such as carboxymethyl cellulose, and whiteners such as titanium dioxide.

Since the denture cream can leave a residue on the dentures or dental prosthesis after cleaning, the denture cream may also contain sweeteners and flavoring agents, including peppermint oil, menthol, saccharin, and anethole.

The purpose of the following examples is to illustrate some embodiments and principles of the invention, without implying a limitation on the scope or spirit of the invention.

EXAMPLES 1 and 2

Two denture creams were prepared having the formulations set out in Table 1. In each instance, 60% of the required amount of water was added to a mixing tank, along with the propylene glycol and 65% of the glycerin. The sodium monofluorophosphate was added to the mixing tank and mixed until dissolved. The sodium saccharin, titanium dioxide, and sodium bicarbonate were then added and mixed to a uniform blend. The polyethylene glycol was then added and mixing continued. The silicon dioxide and hydrated silica were added and mixing continued. At this point, the mixture thickened, so 25% of the water was added to the mixing tank and the resulting blend was mixed under high shear. The carboxymethyl cellulose was separately dispersed in the remaining glycerin and this mixture was added to the mixing tank while mixing continued for an additional twenty (20) minutes until gel formation. The flavors and sweeteners were added to the mixing tank along with sodium lauryl sulfate. After the flavors had been mixed for twenty (20) minutes, the remaining water and calcium peroxide were added and mixed thoroughly for five minutes. The resulting cream was filled into suitable tubes.

EXAMPLE 3

A comparison of the stabilizing effect of various combinations on the peroxide was made by making the denture cream of Examples 1 and 2 using various compounds in place of the sodium monofluorophosphate. The active oxygen in the denture cream was measured after the denture paste was prepared and the denture creams were then stored at 50° C. The active oxygen was measured at one, two and four weeks after storage, and the results are reported in Table 2. These results show that sodium monofluorophosphate is an effective agent and that the other phosphates, while not as effective as sodium monofluorophosphate, also provided some stabilizing effect.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

TABLE 1

Formulations of Examples 1 and 2

| Ingredient | Example 1 (Wt. %) | Example 2 (Wt. %) |
| --- | --- | --- |
| Calcium Peroxide | 0.50 | 0.50 |
| Purified water | 12.00 | 12.00 |
| Glycerin | 21.00 | 20.00 |
| Propylene Glycol | 27.00 | 26.00 |
| Sodium Monofluorophosphate | 0.40 | 0.40 |
| Sodium Bicarbonate | 5.00 | 5.00 |
| Silicon Dioxide | 2.00 | 4.00 |
| Sodium Saccharin | 0.30 | 0.30 |
| Titanium Dioxide | 1.00 | 1.00 |
| Hydrated Silica | 17.00 | 17.00 |
| Polyethylene Glycol 600 | 10.00 | 10.00 |
| Carboxymethyl cellulose 12M31XP | 0.60 | 0.60 |

TABLE 1-continued

Formulations of Examples 1 and 2

| Ingredient | Example 1 (Wt. %) | Example 2 (Wt. %) |
| --- | --- | --- |
| Sodium Lauryl Sulfate | 2.00 | 2.00 |
| Peppermint Oil | 0.82 | 0.78 |
| Menthol | 0.25 | 0.42 |
| Anethole | 0.13 | 0.00 |
| Total | 100.00 | 100.00 |

TABLE 2

Active Oxygen Loss from Example 3

| Active Ingredient | Initial Active Oxygen | % Loss after 1 week | % Loss after 2 weeks | % Loss after 4 weeks |
| --- | --- | --- | --- | --- |
| 0.4% sodium monofluorophosphate | 0.0765% | 2.2% | 6.1% | 21.3% |
| 0.12% sodium fluoride | 0.075% | 62.8% | 88.3% | 89.5% |
| 0.9% tetrapotassium pyrophosphate | 0.072% | 7.9% | 8.7% | 27% |
| 0.45% trisodium phosphate | 0.665% | 20.0% | 22.6% | 40.7% |

What is claimed is:

1. A cream formulation for cleaning dentures and other removable dental prostheses in association with mechanical scrubbing comprising:

(a) a peroxide in an amount sufficient to provide a cleaning effect to said cream;

(b) a bicarbonate in a weight ratio to the peroxide of about 10:1 or less; and (c) a phosphate in a weight ratio to the peroxide of about 1.6:1 or less; and wherein said denture cleansing cream formulation is characterized in having a residual amount of active oxygen of about 80% or more after one week at 50° C.

2. The cream of claim 1, wherein said peroxide is an alkali peroxide.

3. The cream of claim 1, wherein said peroxide is a divalent peroxide.

4. The cream of claim 3, wherein said peroxide is calcium peroxide.

5. The cream of claim 1, wherein said peroxide comprises from about 0.1% to about 10% by weight of the cream.

6. The cream of claim 5, wherein said peroxide comprises from about 0.25% to about 5% by weight of the cream.

7. The cream of claim 6, wherein said peroxide comprises from about 0.5% to about 2.5% by weight of said cream.

8. The cream of claim 1, wherein said bicarbonate is selected from the group consisting of alkali bicarbonates.

9. The cream of claim 8, wherein said bicarbonate is sodium bicarbonate.

10. The cream of claim 1, wherein said bicarbonate comprises more of the denture cream formulation than the peroxide on a weight basis.

11. The cream of claim 10, wherein said bicarbonate is present in said cream in a weight ratio to said peroxide from about 2:1 to about 10:1.

12. The cream of claim 11, wherein said bicarbonate is present in said cream in a weight ratio to said peroxide from about 2:1 to about 5:1.

13. The cream of claim 7, wherein said bicarbonate comprises from about 1% by weight to about 25% by weight of the denture cream.

14. The cream of claim 13, wherein said bicarbonate comprises from about 1% by weight to about 10% by weight of the denture cream.

15. The cream of claim 14, wherein said bicarbonate comprises about 5% by weight of the denture cream.

16. The cream of claim 1, wherein said phosphate is an alkali monofluorophosphate.

17. The cream of claim 1, wherein said alkali monofluorophosphate comprises less of said cream than said bicarbonate on a weight basis.

18. The cream of claim 17, wherein said alkali monofluorophosphate is present in a weight ratio to said peroxide of from about 0.1:1 to about 1.6:1.

19. The cream of claim 18, wherein said alkali monofluorophosphate is present in a weight ratio to said peroxide of from about 0.3:1 to about 0.8:1.

20. The cream of claim 7, wherein said alkali monofluorophosphate comprises from about 0.05% by weight to about 2.5% by weight of said cream.

21. The cream of claim 20, wherein said alkali monofluorophosphate comprises from about 0.4% to about 0.8% by weight of said cream.

22. A method for cleaning dentures or removable dental prostheses comprising the step of mechanically scrubbing said dentures or removable dental prostheses with the cream of claim 1.

* * * * *